(12) United States Patent
Niazi

(10) Patent No.: US 6,235,796 B1
(45) Date of Patent: May 22, 2001

(54) USE OF FLUOROCARBONS FOR THE PREVENTION OF SURGICAL ADHESIONS

(76) Inventor: Sarfaraz K. Niazi, 20 Riverside Dr., Deerfield, IL (US) 60016

( * ) Notice: Subject to any disclaimer, the term of this patent is extended or adjusted under 35 U.S.C. 154(b) by 0 days.

(21) Appl. No.: 09/603,285

(22) Filed: Jun. 26, 2000

(51) Int. Cl.[7] .................................................. A61K 31/025
(52) U.S. Cl. .............................................................. 514/756
(58) Field of Search ..................................... 514/747, 759, 514/756

(56) References Cited

U.S. PATENT DOCUMENTS

| | | | |
|---|---|---|---|
| 3,958,014 | 5/1976 | Watanabe et al. | 424/366 |
| 4,655,222 | 4/1987 | Florez et al. | 128/334 R |
| 5,120,731 | * 6/1992 | Meinert et al. | 514/231.5 |
| 5,658,324 | 8/1997 | Bailey, Sr. et al. | 607/104 |
| 5,733,939 | 3/1998 | Furhman et al. | 514/759 |
| 5,851,544 | * 12/1998 | Penska et al. | 424/401 |
| 5,859,068 | 1/1999 | Wllson | 514/761 |
| 5,861,175 | 1/1999 | Walters et al. | 424/486 |
| 5,882,328 | 3/1999 | Levy et al. | 604/20 |
| 5,906,997 | 5/1999 | Schwartz et al. | 514/781 |
| 5,916,882 | 6/1999 | Jeng | 514/57 |
| 5,928,663 | 7/1999 | Peyman | 424/427 |
| 5,962,006 | 10/1999 | Southard et al. | 424/426 |
| 5,989,918 | 11/1999 | Dietz et al. | 436/63 |
| 6,001,357 | 12/1999 | Wong et al. | 424/145 |
| 6,034,140 | 3/2000 | Schwartz et al. | 514/781 |
| 6,037,331 | 3/2000 | Shalaby et al. | 514/54 |

FOREIGN PATENT DOCUMENTS

99/04828 * 2/1999 (WO).

OTHER PUBLICATIONS

Stedman's Medical Dictionary, 472 and 840, 1995.*
Ellis, *Surg. Gynecol. Obstet.* 133:497, 1971.
Holtz, *Fertil. Steril.* 41:497, 1984.
Diamond and Hershlag, *Prg. Clin. Biol. Res.* 358:23, 1990.

* cited by examiner

*Primary Examiner*—Phyllis G. Spivack
(74) *Attorney, Agent, or Firm*—Welsh & Katz, Ltd.

(57) ABSTRACT

Method for the prevention and inhibition of adhesion between tissues comprising the use of fluorocarbons are disclosed. The method provides for the introduction of a fluorocarbon into the surgical site of a mammalian body, such as a human, to minimize friction and enhance the mobility of the surrounding tissues and organs. The fluorocarbons introduced may be in various forms including liquid and emulsions, and provides a coating, film or barrier thereby reducing the surface tension associated after surgery. The subject invention further discloses the use of perfluorodecalin as a preferred fluorocarbon compound used as the primary anti-adhesion agent.

10 Claims, No Drawings

USE OF FLUOROCARBONS FOR THE PREVENTION OF SURGICAL ADHESIONS

FIELD OF THE INVENTION

This invention relates generally to the prevention and inhibition of adhesions between tissues formed after surgery. More particularly, this invention relates to an inert fluorocarbon composition for the prevention of adhesions resulting from surgical procedures in a mammal.

BACKGROUND OF THE INVENTION

Adhesions are fibrous bands of tissue connecting one or more organ sites within the body. More specifically, adhesions as concerned here occur as a result of post-surgical tissues growing together either between layers of adjacent bodily tissue or between tissues and internal organs. Adhesions can form during the healing which follows surgical procedures, and when present, adhesions can prevent the normal motions of those tissues and organs with respect to their neighboring structures.

Although the inventor does not wish to be bound by any particular theory of the invention, it is believed that the adhesions occur when the tissue becomes injured. Typically injury to, or ischemia of, serosal tissue results in an increased immune response at the site, with a subsequent release of serosanguinous exudate resulting in fibrin deposition at the injured site. Adhesions form as a result of the induced inflammatory response in combination with an impaired ability to lyse such fibrin deposits. Generally, in normal tissues the tissue surface produces tissue plasminogin activators (t-PA) which converts inactive plasminogen to plasmin. This protolytic mechanism of plasmin dissolves fibrin deposits and thus prevents adhesion formation. However, ischemic injury to serosal surfaces retards t-PA production. Reduced t-PA production results in excessive fibrin accumulation at the injured site. Such fibrin deposits serve as a matrix for fibroblastic infiltration and proliferation. Eventually, collegenous bands contract as healing proceeds and thereby limit movement of the affected organ or organs.

Consequently, adhesion formation results generally from thoracic, abdominal, lumbar and/or gynecological surgeries and represents a significant clinical problem across many different fields of medicine. Postoperative adhesions occur in 70–95% of all cases. For example, post-surgical peritoneal adhesions are one of the leading causes of intestinal blockage or obstruction (Ellis, *Surg. Gynecol. Obstet.* 133:497, 1971), and are also of great concern to surgeons who attempt to improve fertility in women through reconstruction. Pelvic adhesions can impair fertility by interfering with the ability of the fallopian tubes to pick up the ovum (Holtz, *Fertil. Steril.* 41:497, 1984; Diamond and Hershlag, Prg. *Clin. Biol. Res.* 358:23, 1990). The formation of permanent adhesions in tendons and joints is a major cause of decreased mobility and chronic pain.

Over the years many different strategies have been employed to prevent the formation of adhesions. Good operating techniques, gentle handling of tissues, lavage of the peritoneal cavity, hemostasis, and irrigation will prevent the formation of adhesions to a certain extent, however, these procedures never completely inhibit adhesion formation after surgery. Therefore, numerous approaches to elimination of adhesion formation have been attempted, with limited success in most cases. Approaches have included the mechanical separation of tissues or the administration of pharmacological agents.

A mechanical separation or barrier material, is typically applied as a sheet or film and sutured in place to prevent the deposition of fibrin. Examples of such materials include oxidized cellulose membranes, polytetrafluoroethylene, or hyaluronic acid. However, most such barrier materials have proven unsuccessful. For example, Interceed™ Barrier, and oxidized cellulose is very difficult to place and can only be applied to a non-bleeding site. Gore-Tex™, poses another problem by having to always be sutured in place and must eventually be removed. This removal process further introduces additional potential trauma or injury to the tissue. Seprafilm™, a hyaluronic acid film, becomes very brittle and has a tendency to crack. This tendency results in an inadequate barrier between the injured tissue and the surrounding tissue, which in turn increases the chances of adhesion formations.

Another approach used to prevent the formation of adhesions is the use of pharmaceutical agents. Typical pharmaceutical agents include corticosteroids and nonsteroidal anti-inflammatory agents (to inhibit fibroblastic proliferation); heparin and sodium citrate (to prevent fibrin deposition); and pentoxifyline, rt-PA, urokinase and streptokinase (to promote fibrinolysis). Unfortunately, the success of pharmaceutical agents in preventing adhesion formation has been limited, due to the difficulty of directing the drugs to the injury with systemic administration.

In summary, several approaches have been explored, but none have been able to achieve the desired system, which is successful in preventing adhesion formation after surgery, can be applied easily to the surgical site and still be effective. Additionally, the ability of an anti-adhesion composition that remains intact at the surgical site during the initial stages of critical wound healing is also desirable. Moreover, a system that allows for local administration of a composition, which prevent adhesion formation would be most desirable.

SUMMARY OF THE INVENTION

The present invention is directed to an inert, non-toxic composition that is used during surgery to prevent the tissues and organs from forming adhesions after surgery. More particularly, the invention comprises the introduction of fluorocarbons into the surgical site for the purpose of preventing and inhibiting tissue and organ adhesions, and specifically a perfluorocarborn such as perfluorodecalin.

DETAILED DESCRIPTION OF A PREFERRED EMBODIMENT

The present invention provides a method of prevention and inhibition of tissue and organ adhesions associated with abdominal, pelvic or pleural surgeries by administration of fluorocarbons to the site of the surgery.

In essence, fluorocarbons have long been utilized successfully in a number of medical applications. Many fluorocarbon molecules are generally characterized as non-toxic, very chemically inert, have a low body-retention time and are chemically and thermally stable substances. These physical properties adapt themselves well to numerous medical applications. In prior art, fluorocarbon liquids have been proposed for the treatment of respiratory distress syndrome by removal of lung debris, inflammatory cells and materials by lavage, and by facilitating oxygen delivery. In contrast, however, the present invention uses fluorocarbons directed toward prevention and inhibition of tissue and organ adhesion by facilitating a coating, film or barrier thereby reducing the surface tension associated with tissues after surgery. In other words, the fluorocarbon of the subject invention is used as a primary anti-adhesion agent.

When fluorocarbons are introduced or administered to the surgical site in accordance with the present invention some or all of it preferably adheres to the surface of the tissue forming a slick, smooth fluorocarbon film that minimizes friction and enhances the mobility of the tissue. The introduced fluorocarbon acts as a film or barrier between adjacent tissues, and allows the surrounding tissue and organs within the surgical site to retain their mobility and not adhere together.

Fluorocarbon molecules used in the present invention may have various forms. Typically, the fluorocarbon is a liquid or gas at room temperature (25° C.). Preferably, the fluorocarbon used is a cyclic structure having from about 8, 10, 12 or 14 carbon atoms, and having 1 to 3 rings. More preferably, a fluorocarbon comprising perfluorinated compounds are used in the present invention and chosen for their low water solubility, non-toxicity, high density or vicosity, surface tension and spreading coefficient. In the selected embodiment of the invention the fluorocarbon used is perfluorodecalin. Perfluorodecalin is a polycyclic fluorocarbon and is useful in the present invention because of its low vapor pressure properties, desirable viscosity and density characteristics, and longer residence time thus allowing for a therapeutic effect lasting a longer period of time in the surgical site. Mixtures of fluorocarbons are also contemplated. Additionally "fluorocarbons" not listed herein, but having those properties described in this disclosure that would lend themselves to use in accordance with the present invention are also contemplated.

The fluorocarbons used in the present invention may be used as a neat liquid composition, or as emulsions. Emulsions typically include emulsifying agents and osmotic agents, together with buffers and electrolytes. Preferably, emulsions are a combination of a fluorocarbon and at least one surfactant. The fluorocarbon emulsions may be selected from a wide range of suitable emulsions.

Although concentrations as low as 5% w/v are contemplated, in a preferred embodiment the concentrations are at least 10%, preferably at least 14–15%. Emulsions of up to 30% are also contemplated.

The emulsion can be applied to a tissue of a mammal, such as a human, in any convenient manner. While the liquid may be simply poured into the open surgical site, it is preferred that the formulation have a consistency wherein it can be sprayed into tissue using a topical spray apparatus thereby forming a uniform, thin protective film over the exposed tissues and organs.

Working Example

In the following example an emulsion is prepared to form the fluorocarbon composition used in experiment. Perfluorodecalin dosage form was prepared by emulsifying 14% perfluorodecalin using Pluronic F-68 (polyoxamer 188) and soya lecithin in a micronizing mill and subsequently sterilized. Perfluorodecalin is the preferred fluorocarbon used in the Example, however, this invention is not limited to this Example, but can be practiced in any equivalent fashion without departing from the invention.

EXAMPLE 1

Fifty-one sexually mature female, New Zealand white rabbits, weighing between 3.5 and 4.5 kg were selected for the study. They were maintained in isolation for a period of two weeks on a standardized diet, light and other environmental factors prior to the surgical procedures. Operations were preformed under ketamine anesthesia (80 mg/mL) and acepromazine (1.6 mg/ML) given subcutaneously following 12 to 18 hours of preoperative starvation. No antibiotics were used.

Two laparotomies were done, four weeks apart. For the first laparotomy, a midline abdominal incision was made after the surgeon has cleaned all visible talc from his gloves. All animals underwent bilateral transection of the tubocornual junction with subsequent reanastomosis. A midline, lower abdominal incision was used to approach the fallopian tubes. Tubocornual anastomosis was performed using microsurgical techniques. No postoperative stents were left in position and hemostatis was considered to be of paramount importance. Prior to closure of the anterior abdominal wall, the peritoneal cavity was gently cleansed of all blood clots or debris with warm normal saline irrigation. All animals were then randomly allocated according to a previously calculated table of randomisation to any one of the following three groups:

TABLE 1

| | |
|---|---|
| Group I: | The peritoneal cavity was filled with 30–50 mL of perfluorodecalin emulsion. |
| Group II: | The peritoneal cavity was filled with 30–50 mL of normal saline. |
| Group III: | No fluids added to the peritoneal cavity. |

Four weeks after the surgery, a second laparatomy was performed. The pelvic contents and both anantomotic sites were examined for the degree of pelvic adhesions that were assessed according to the following scale:

TABLE 2

| | |
|---|---|
| Absent: | None under 5X magnification: 0 |
| Mild: | Microscopic adhesions < 5 mm form anastomosis: 1 |
| Moderate: | Naked eye including adjacent oviduct or mesentery: 2 |
| Severe: | Extension to uterus, bladder, intestine, or abdominal wall: 3 |

TABLE 3

Results
Percent of survivors showing adhesion types:

| Adhesions | Group I | Group II | Group III |
|---|---|---|---|
| None | 80% | 20% | 10% |
| Mild/Moderate | 20% | 60% | 70% |
| Severe | 0% | 20% | 20% |

Of the 51 animals seven died, three after the first surgery and four after the second laparotomy.

While the invention will be farther described in connection with certain preferred embodiments, it is not intended to limit the invention to those embodiments. On the contrary, it is intended to cover all alternatives, modifications and equivalents as may be included within the spirit and scope of the invention.

What is claimed is:

1. A method for preventing or inhibiting the formation of adhesions in a surgical site comprising the step of locally administering to said surgical site on internal surfaces within said surgical site an effective adhesion preventing amount of an inert and non-toxic polycyclic fluorocarbon forming a lubricated barrier between said internal surfaces.

2. The method of claim 1, wherein said inert and non-toxic material is a form of an emulsion.

3. The method of claim 2, wherein said inert and non-toxic material is in the form of a spray.

4. The method of claim 1 wherein said inert and non-toxic material is perfluorodecalin.

5. The method of claim 4 wherein said perfluorodecalin is in the form of an emulsion.

6. A method for preventing or inhibiting the formation of adhesions in a surgical site comprising the step of administering locally to said surgical site on internal surfaces within said surgical site an effective adhesion preventing amount of perfluorodecalin emulsion forming a lubricated barrier between said internal surfaces.

7. A method for preventing or inhibiting the formation of adhesions in a surgical site comprising the step of topically spraying on said surgical site on internal surfaces within said surgical site an effective adhesion preventing amount of perfluorodecalin forming a lubricated barrier between said internal surfaces.

8. A method of claim 7 wherein said surgical site is a peritoneal cavity.

9. A method of claim 7 wherein said surgical site is an abdominal or pelvic region.

10. A method of claim 7 wherein said surgical site is a pleura region.

\* \* \* \* \*